United States Patent
Ekman et al.

(10) Patent No.: US 9,694,138 B2
(45) Date of Patent: Jul. 4, 2017

(54) SAFETY DEVICE FOR A PRE-FILLED SYRINGE, INJECTION DEVICE AND INJECTION KIT

(75) Inventors: Matthew Ekman, Macclesfield (GB); Christopher James Smith, Holmes Chapel (GB); Troy Baker, St. Asaph (GB); Graham Wilson, Flint (GB); Gareth Roberts, Wrexham (GB); John Slemmen, Wallasey (GB)

(73) Assignee: Sanofi-Anetis Deutschland GMBH, Frankfurt am Main (DE)

( * ) Notice: Subject to any disclaimer, the term of this patent is extended or adjusted under 35 U.S.C. 154(b) by 1091 days.

(21) Appl. No.: 13/808,023

(22) PCT Filed: Jun. 21, 2011

(86) PCT No.: PCT/EP2011/060316
§ 371 (c)(1),
(2), (4) Date: Aug. 23, 2013

(87) PCT Pub. No.: WO2012/000832
PCT Pub. Date: Jan. 5, 2012

(65) Prior Publication Data
US 2013/0331794 A1    Dec. 12, 2013

(30) Foreign Application Priority Data
Jul. 2, 2010   (EP) .................................. 10168314

(51) Int. Cl.
*A61M 5/32*   (2006.01)
*A61M 5/28*   (2006.01)

(52) U.S. Cl.
CPC .......... *A61M 5/3204* (2013.01); *A61M 5/326* (2013.01); *A61M 5/3272* (2013.01);
(Continued)

(58) Field of Classification Search
CPC .............. A61M 5/3204; A61M 5/3272; A61M 5/3271; A61M 2005/3267
See application file for complete search history.

(56) References Cited

U.S. PATENT DOCUMENTS 5,498,243 A * 3/1996 Vallelunga .......... A61M 5/3243
                                                  604/187
5,599,309 A * 2/1997 Marshall ............. A61M 5/2033
                                                  604/117
(Continued)

FOREIGN PATENT DOCUMENTS

EP      1362609 A1    11/2003
FR      2884722       10/2006
(Continued)

OTHER PUBLICATIONS

Form PCT/IB/326, Notification Concerning Transmittal of International Preliminary Report on Patentability, Jan. 2013.
(Continued)

*Primary Examiner* — Nathan R Price
*Assistant Examiner* — Weng Lee
(74) *Attorney, Agent, or Firm* — Fish & Richardson P.C.

(57) ABSTRACT

According to the invention, a safety device for a pre-filled syringe comprises a hollow support body to retain the pre-filled syringe therein, a hollow needle shield that is slidable relative to the support body and guiding means for guiding the movement of the needle shield relative to the support body. The guiding means comprise a guide pin, a guide track and a cut-out adjacent to the guide track. The guide pin protrudes into the guide track and moves within and along the guide track when the needle shield is slid relative to the support body. The cut-out allows a side wall of the guide track to be deflected in a lateral direction perpendicular to a central axis of the safety device.

20 Claims, 5 Drawing Sheets

(52) U.S. Cl.
CPC ............ *A61M 5/28* (2013.01); *A61M 5/3287* (2013.01); *A61M 2005/3267* (2013.01)

(56) References Cited

U.S. PATENT DOCUMENTS

| | | | | |
|---|---|---|---|---|
| 2002/0004652 A1* | 1/2002 | Asbaghi | ................ | A61M 5/326 604/242 |
| 2003/0125677 A1* | 7/2003 | Swenson | .............. | A61B 17/205 604/263 |
| 2004/0111064 A1* | 6/2004 | Asbaghi | ................ | A61M 5/3272 604/198 |
| 2005/0165353 A1* | 7/2005 | Pessin | ................. | A61M 5/3272 604/110 |
| 2005/0187522 A1* | 8/2005 | Miller | ................. | A61M 5/3272 604/198 |
| 2008/0167611 A1* | 7/2008 | Miller | ................. | A61M 5/3257 604/110 |
| 2011/0319832 A1* | 12/2011 | Chun | .................... | A61M 5/326 604/198 |

FOREIGN PATENT DOCUMENTS

| | | | | |
|---|---|---|---|---|
| IT | EP 1362609 A1 * | 11/2003 | ............ | A61M 5/326 |
| WO | 03045481 A1 | 6/2003 | | |
| WO | WO2006/111861 | 10/2006 | | |

OTHER PUBLICATIONS

International Search Report and Written Opinion in International Application No. PCT/EP2011/060316, mailed Sep. 16, 2011, 11 pages.
International Preliminary Report on Patentability in International Application No. PCT/EP2011/060316, dated Jan. 8, 2013, 8 pages.

* cited by examiner

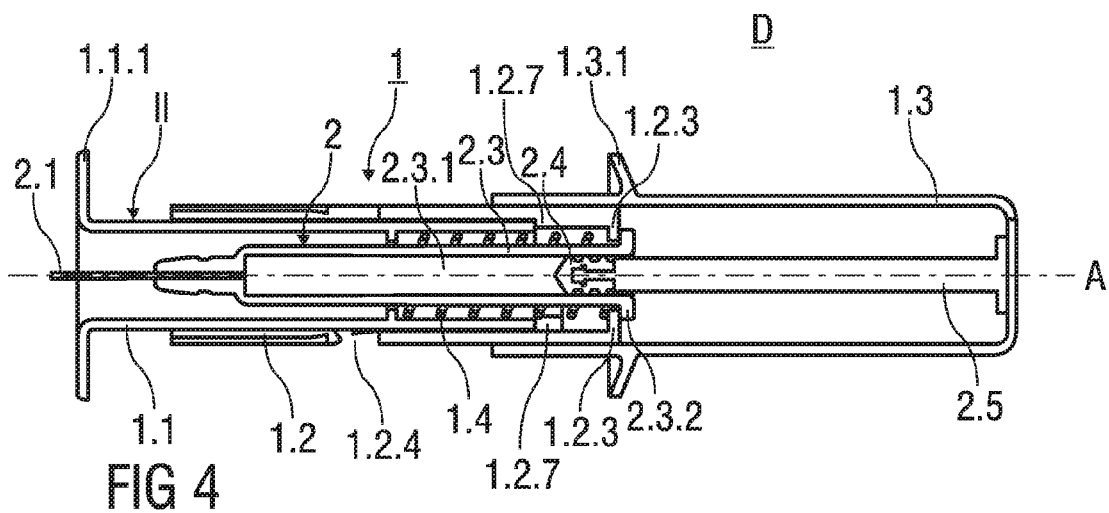

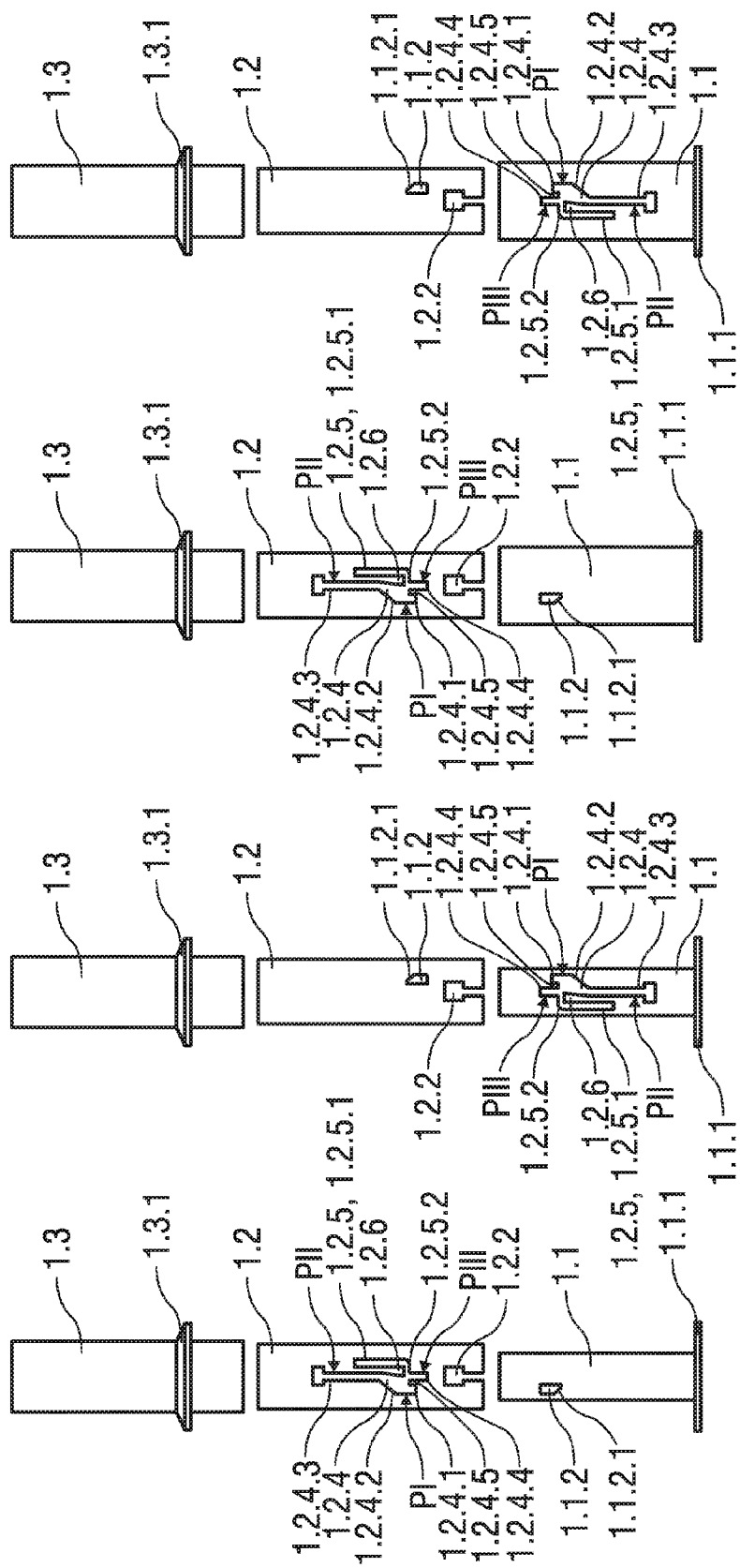

SAFETY DEVICE FOR A PRE-FILLED SYRINGE, INJECTION DEVICE AND INJECTION KIT

CROSS REFERENCE TO RELATED APPLICATIONS

The present application is a U.S. National Phase Application pursuant to 35 U.S.C. §371 of International Application No. PCT/EP2011/060316 filed Jun. 21, 2011, which claims priority to European Patent Application No. 10168314.2 filed Jul. 2, 2010. The entire disclosure contents of these applications are herewith incorporated by reference into the present application.

FIELD OF INVENTION

The present invention relates to safety devices that provide needle safety and more particularly to safety devices for pre-filled syringes. The safety device is adapted to avoid accidental needle stick injuries and needle injuries before, during and after an injection of a medication or drug contained in the pre-filled syringe. In particular, the safety device provides needle safety for a subcutaneous self-administrated injection or for an injection administered by a health-care professional. The present invention further relates to injection devices comprising a pre-filled syringe.

BACKGROUND

Pre-filled syringes that are filled with a selected dosage of a medication are well known injection devices for administering the medication to a patient. Safety devices for covering a needle of a pre-filled syringe before and after use are also well known. Typically, these devices comprise a needle shield that is either manually moved or moved by the action of a relaxing spring to surround the needle. However, there is a need for safety devices comprising a low number of components.

SUMMARY

It is an object of the present invention to provide an improved safety device for a pre-filled syringe.

It is a further object of the invention to provide an improved injection device comprising a pre-filled syringe that is safe to handle and in particular prevents accidental needle stick injuries.

The object is achieved by a safety device according to claim 1 and by an injection device according to claim 13.

Preferred embodiments are subject of the dependant claims.

In the context of this specification, the terms distal and proximal are defined from the point of view of a person performing an injection. Consequently, a distal direction refers to a direction pointing towards the body of a patient receiving an injection and a distal end defines an end of an element that is directed towards the body of the patient. Respectively, the proximal end of an element or the proximal direction is directed away from the body of the patient receiving the injection and opposite to the distal end or distal direction.

According to the invention, a safety device for a pre-filled syringe comprises a hollow support body to retain the pre-filled syringe therein, a hollow needle shield that is slidable relative to the support body and guiding means for guiding the movement of the needle shield relative to the support body. The guiding means comprise a guide pin, a guide track and a cut-out adjacent to the guide track. The guide pin protrudes into the guide track and moves within and along the guide track when the needle shield is slid relative to the support body. The cut-out allows a side wall of the guide track to be deflected in a lateral direction perpendicular to a central axis of the safety device.

The needle shield is slid relative to the support body to expose and cover in particular a hypodermic needle of a pre-filled syringe retained within the support body. The guide pin accommodated in the guide track guides the movement of the needle shield, whereas the needle shield is retained in position by the guide pin interacting with the guide track. The deflectable side wall of the guide track acts as a no-return feature that restricts the movement of the guide pin within the guide track. The guide pin is restricted to move along the guide track only during the first use of the safety device. A subsequent use of the safety device is efficiently prevented, which reduces the risk of an infection caused by a needle stick injury with a contaminated hypodermic needle.

The safety device is preferably used in combination with disposable pre-filled syringes.

The guide pin is connected to either the needle shield or the support body. The guide track is formed into the other of the needle shield or the support body. Therefore, it is within the scope of the present invention that the safety device comprises a support body with a guide track and a needle shield with a guide pin, or alternatively, that the guide pin is connected to the support body and a guide track is formed into the needle shield.

An axial section of the cut-out extends parallel to a first section of the guide track and parallel to the central axis. The needle shield is slidably arranged with respect to the support body to cover and expose the hypodermic needle. The guide pin jointly moves with the needle shield along the guide track. The cut-out adjacent to the guide track provides a simple mechanism for the side wall to be deflected in a lateral direction, which in turn introduces the no-return feature to the guide track. No additional parts are required that prevent the re-usage of the safety device. The safety device thus comprises just a low number of components and can be cost-efficiently mass-produced.

According to a possible embodiment, the needle shield is rotated within the support body about an angular segment by the movement of the guide pin along the guide track, whereby the needle shield is moved relative to the support body to expose and cover the hypodermic needle received within the support body. The needle shield rotates with respect to the support body when the needle shield is moved between an initial position, in which the needle shield protrudes the support body, and a retracted position, in which the needle shield is substantially received within the support body.

Alternatively, the support body may be substantially received within the needle shield when the needle shield is in the retracted position.

Additionally or alternatively, the needle shield may rotate with respect to the support body when the needle shield is moved from the retracted position to an advanced position. The safety device avoids complicated mechanisms to retain the needle shield into position that are prone to malfunction and ensures a reliable use during an injection delivering a medication beneath the skin of a patient.

The needle shield is retained in the initial position by the guide pin being retained in a start position within the guide track. The guide pin in the start position abuts a first U-shaped indentation of the guide track in a distal and in the lateral direction and an inclined camming surface in a proximal direction to releasably retain the needle shield in the initial position. As the needle shield protrudes the support body in the initial position, the safety device avoids inadvertent needle stick injuries prior to use of the safety device when the pre-filled syringe is retained in the support body.

In a possible embodiment, the needle shield is made from an opaque plastics material, so that the hypodermic needle is shed from the view of a user prior the injection. This in particular reduces the fear of performing self-administered injections that, for example, patients suffering from diabetes frequently have to carry out.

According to an alternative embodiment, the needle shield is made from a transparent plastics material. A healthcare professional that uses the safety device thus can visually confirm the correct placement of the hypodermic needle penetrating the skin of the patient, even when the hypodermic needle is surrounded by the needle shield.

As the safety device is both suited for self-administered injections and injections carried out by a healthcare professional, the person referred to as the user or the patient may be one and the same person.

The needle shield protrudes the support body in the advanced position. The needle shield is permanently retained in the advanced position by the guide pin being retained in and locked to an end position located at a distal end of the guide track. The guide pin in the end position abuts a second U-shaped indentation of the guide track in the distal and in the lateral direction and a distal end of the side wall in the proximal direction to lock the needle shield to the advanced position. The needle shield in the advanced position protrudes the support body. The safety device thus provides needle safety after an injection, so that accidental needle stick injuries with contaminated hypodermic needles are prevented.

The side wall of the guide track is laterally deflected when the guide pin enters the end position. As already described herein above, the lateral deflectable side wall introduces the no-return feature to the guide track. The guide pin is thus permanently retained and locked to the end position after the first use of the device, so that the needle shield is retained and locked to the advanced position. In particular, a proximal movement of the needle shield is prevented as soon as the guide pin reaches the end position. An additional interaction of the user performing the injection stroke is not required to lock the needle shield to the advanced position.

In a preferred embodiment, the guide pin comprises a tapered end that abuts an arcuate section of the guide track to redirect the guide pin into the end position. This particular shape of the guide pin and the arcuate section of the guide track minimize friction between these parts, so that the guide pin reliably enters the end position to lock the needle shield to the advanced position.

In yet another preferred embodiment of the invention, the needle shield comprises a skin-contact flange that is designed to rest on top of a skin surface of the patient receiving the medication. The skin-contact flange facilitates proper placement of the safety device during, in particular, a subcutaneous or intramuscular injection.

According to yet another embodiment, the needle shield is retractable into the support body from the initial position to the retracted position, in which the needle shield is substantially received within the support body but still protrudes the support body by an axial length that is limited by an inwardly protruding inner rib of the support body. This in turn limits a penetration depth of the hypodermic needle into the skin of the patient when the pre-filled syringe is retained within the support body of the safety device, as the skin-contact flange rests onto the skin surface of the patient during the injection. The safety device is safe and easy to handle even for inexperienced users and avoids inadvertent injuries caused by improperly executed injections.

The support body is retained within and slidable with respect to an outer body in a distal direction, whereas the outer body is slid relative to the support body in a distal direction to expel the medication contained in the pre-filled syringe. The outer body comprises at least one locking catch that engages a locking recess formed into the support body to irreversibly lock the outer body relative to the support body at the end of the injection stroke, whereby the support body is substantially received within the outer body. A subsequent proximal movement of the outer body is prevented and the safety device prevented from being re-used.

An injection device comprises a safety device with a pre-filled syringe retained in the support body of the safety device. The pre-filled syringe is of conventional design and comprises the hypodermic needle attached to a distal end of the pre-filled syringe, a barrel with an inner cavity in fluid communication with the hypodermic needle, a piston fluid-tightly sealing a proximal end of the inner cavity and a piston rod protruding a proximal end of the barrel. The piston is movable by actuating the piston rod in at least a distal direction.

The pre-filled syringe is retained within the support body of the safety device, so that the hypodermic needle protrudes the distal end of the support body. The hypodermic needle is surrounded by the needle shield in the initial position and in the advanced position and exposed in the retracted position. The injection device comprising the pre-filled syringe and the safety device combines the aforementioned advantages and avoids inadvertent needle sticks before, during and after an injection delivering the medication beneath the skin of patient.

The injection device is in particular designed to differ in appearance from standard syringes to reduce a possible fear of performing a self-administered injection.

According to a possible embodiment, the penetration depth of the hypodermic needle is limited by the inner rib when the needle shield is in the retracted position, so that a self-administered injection can be safely carried out.

An injection kit comprises the injection device and a substantially tubular needle cap remover that is insertable into the needle shield from a distal end. The needle cap remover clamps to a needle cap frictionally affixed to a distal end of the pre-filled syringe prior to use of the injection device. In particular, the needle cap remover facilitates the removal of the needle cap when the needle shield surrounds the needle cap in the initial position. The needle cap is removable from being affixed to the distal end of the pre-filled syringe by pulling the needle cap remover in the distal direction.

Alternatively, the injection device is shipped and delivered to an end user with a needle cap remover affixed to the needle cap, whereas the needle cap remover protrudes the needle shield in the distal direction to facilitate removal of the needle cap.

Further scope of applicability of the present invention will become apparent from the detailed description given hereinafter. However, it should be understood that the detailed description and specific examples, while indicating possible embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will be better understood from the detailed description given in the following. The accompanying drawings are given for illustrative purposes only and do not limit the scope of the present invention.

FIG. 4 shows a sectional view of an injection device with a safety device, wherein a needle shield is retained in a retracted position.

FIG. 5 shows a sectional view of an injection device with a safety device, wherein a needle shield is retained in an advanced position.

FIGS. 7A to D show exploded views of alternative embodiments for a safety device.

Corresponding parts are marked with the same reference symbols in all figures.

DETAILED DESCRIPTION

Figure 1:
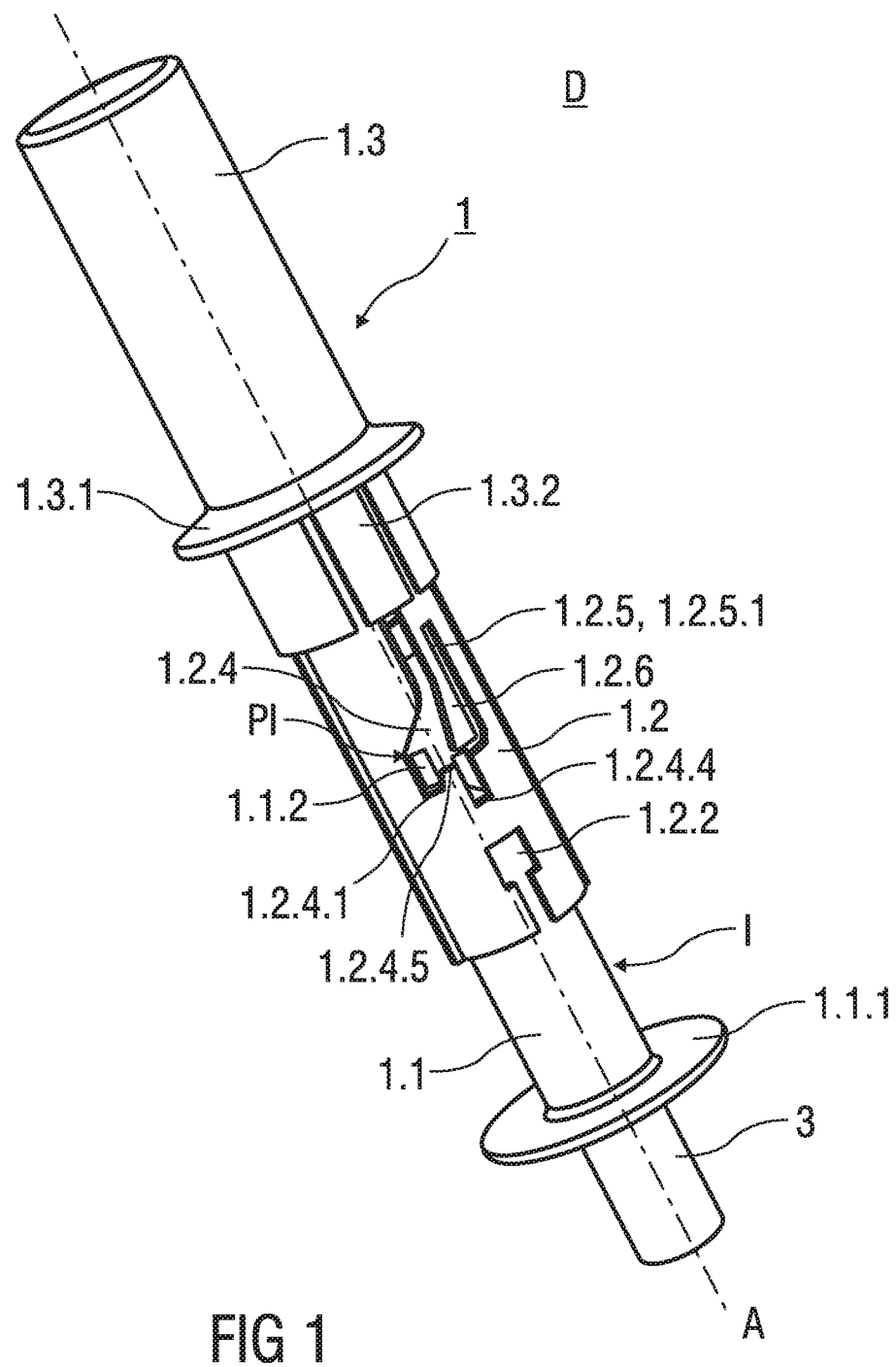
FIG. 1 shows a perspective view of an injection device comprising a safety device and a pre-filled syringe.

FIG. 1 shows an injection device D comprising a safety device 1 and a pre-filled syringe 2. The injection device D is in a packaged state as it would be presented to a user performing an injection. The safety device 1 comprises a substantially cylindrical and hollow needle shield 1.1. The needle shield 1.1 is received within a substantially cylindrical and hollow support body 1.2, whereas the needle shield 1.1 is slidable with respect to the support body 1.2. Prior to use of the safety device 1, the needle shield 1.1 is retained in an initial position I, wherein the needle shield 1.1 protrudes the support body 1.2.

Alternatively, the substantial cylindrical needle shield 1.1 comprises a radial diameter that is sized to substantially receive the support body 1.2. In this alternative embodiment the support body 1.2 slides into the needle shield 1.1 when the needle shield 1.1 is moved from the initial position I to a retracted position II.

The safety device 1 comprises an essentially cylindrical and hollow outer body 1.3 with an open distal and a closed proximal end. The proximal end of the support body 1.2 is received within the open distal end of the outer body 1.3, whereas the outer body 1.3 is slidable with respect to the support body 1.2 in a distal direction to substantially receive the support body 1.2 within the outer body 1.3.

Preferably, the needle shield 1.1, the support body 1.2 and the outer body 1.3 are made from a plastics material.

A circumferential and outwardly protruding hand flange 1.3.1 is integrally formed to an exterior surface of the outer body 1.3 close to its distal end.

Two diametrical opposing longitudinal tongues 1.2.1 are formed to opposite sides of the support body 1.2. Each longitudinal tongue 1.2.1 protrudes radial outwardly and extends over an axial length parallel to a central axis A of the substantially cylindrical support body 1.2. The longitudinal tongue 1.2.1 is received in a corresponding longitudinal groove (not illustrated) formed into an interior surface of the outer body 1.3. The outer body 1.3 is slidable relative to the support body 1.2 in the distal direction to perform an injection stroke. A relative rotation of the support body 1.2 and the outer body 1.3 during the injection stroke is prevented by the longitudinal groove 1.3.1 receiving the longitudinal tongue 1.2.1 of the support body 1.2.

The needle shield 1.1 comprises a circumferential skin-contact flange 1.1.1 at its distal end. The skin-contact flange 1.1.1 is adapted to be pressed against the skin of a patient and protrudes radial outwardly and perpendicular to a central axis A of the safety device 1. Edges of the skin-contact flange 1.1.1 that come into contact with the skin of the patient are rounded to avoid injuries. The skin-contact flange 1.1.1 has a central opening centred on the central axis A of the safety device 1. The skin-contact flange 1.1.1 is integral part of the needle shield 1.1, or alternatively, a separate part attached to the needle shield 1.1 that is made from a plastics material.

Figure 2:
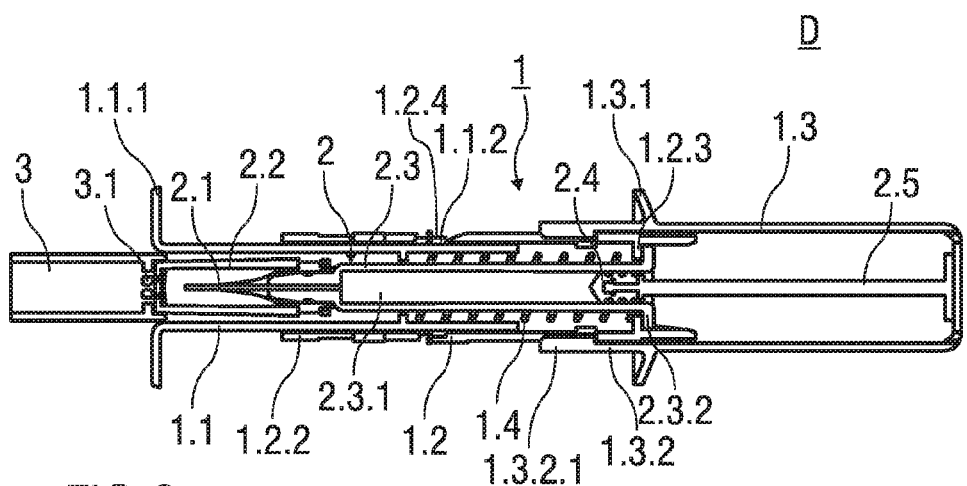
FIG. 2 shows a sectional view of an injection device prior to use.

The injection device D comprises the safety device 1 with the pre-filled syringe 2 retained within the support body 1.2. FIG. 2 shows the pre-filled syringe 2 received within the support body 1.2 that comprises a hypodermic needle 2.1 covered by a needle cap 2.2 frictionally affixed to a distal end of a barrel 2.3. The barrel 2.3 has an inner cavity 2.3.1 containing a medication. The inner cavity 2.3.1 is in fluid communication with the hypodermic needle 2.1. A proximal end of the inner cavity 2.3.1 is fluid-tightly sealed by a piston 2.4 that is connected to piston rod 2.5. The piston 2.4 is movable in at least the distal direction by actuating the piston rod 2.5 protruding the barrel 2.3 in the proximal direction. The barrel 2.3 of the pre-filled syringe 2 comprises a barrel collar 2.3.2 that abuts a radial inwardly protruding inner surface 1.2.3 of the support body 1.2 at its proximal end affixing the pre-filled syringe 2 to the support body 1.2.

Alternatively, the support body 1.2 may comprise retaining means like, for example, a snap-lock type connection that engages the barrel collar 2.3.2 to retain the pre-filled syringe 2 within the support body 1.2.

The pre-filled syringe 2 is retained within the support body 1.2, whereby the hypodermic needle 2.1 protrudes the support body 1.2 in the distal direction.

In the packaged state as shown in FIGS. 1 and 2, the hypodermic needle 2.1 is covered by a needle cap 2.2 that is surrounded by the needle shield 1.1 prior to use of the injection device D. The needle cap 2.2 is preferably at least partially made from a plastics material like rubber. The width of the central opening of the skin contact flange 1.1.1 corresponds to an outer diameter of the needle cap 2.2. A needle cap remover 3 is inserted into the central opening of the skin contact flange 1.1.1 and protrudes the skin-contact flange 1.1.1 in a distal direction, so that the user can easily remove the needle cap 2.2 from the pre-filled syringe 2 by pulling the needle cap remover 3 in the distal direction. The needle cap remover 3 comprises clamp means 3.1 that clamp to a distal end of the needle cap 2.2.

Alternatively, the injection device D is shipped and delivered to an end-user with a needle cap remover 3 attached to the distal end of the needle cap 2.2 retained within the safety device 1, so that the needle cap remover 3 protrudes the needle shield 1.1 in the distal direction.

As can be seen in FIGS. 1 and 2, a clamp arm 1.3.2 is formed into the substantially cylindrical outer body 1.3 that is deflectable in a radial direction perpendicular to the central axis A. As best seen in FIG. 2, the clamp arm 1.3.2 comprises an inwardly protruding locking catch 1.3.2.1 that is sized to fit into a locking recess 1.2.2 formed into the support body 1.2 in proximity of a distal end of the support body 1.2.

Figure 3:
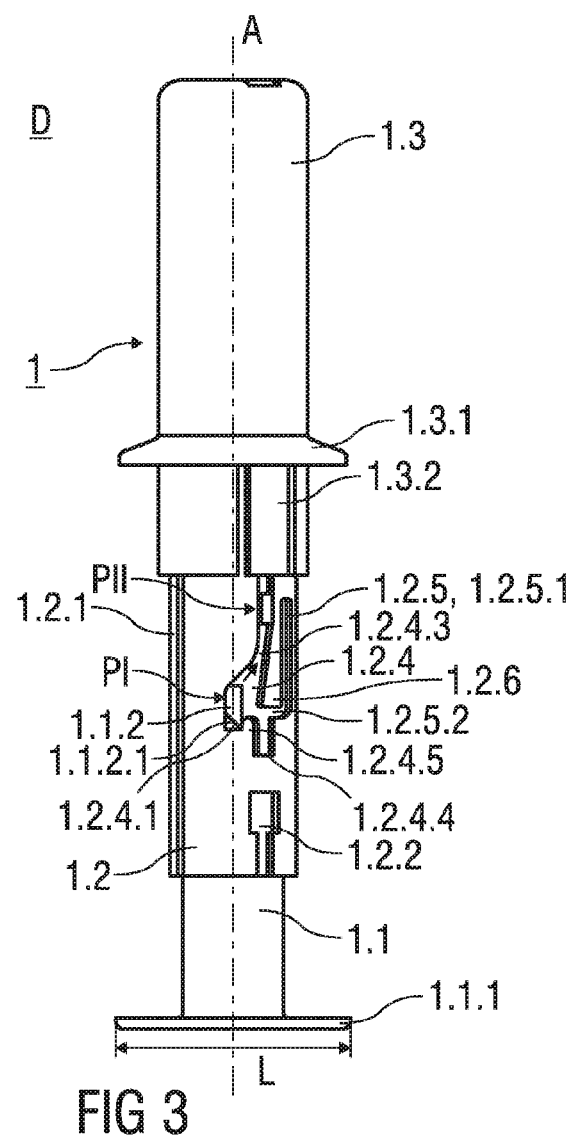
FIG. 3 shows a side view of an injection device, wherein a needle shield of a safety device is retained in an initial position.

As illustrated in FIGS. 1 and 3, a guide track 1.2.4 is formed into the support body 1.2 that accommodates a guide pin 1.1.2. The guide pin 1.1.2 is formed to an exterior surface of the needle shield 1.1 and protrudes the needle shield 1.1 radial outwardly and into the guide track 1.2.4. The needle shield 1.1 is retained in position by the guide pin 1.1.2 being retained in various positions within the guide track 1.2.4.

The guide pin 1.1.2 comprises a tapered end 1.1.2.1 facing in the distal direction.

FIGS. 1 to 3 show the needle shield 1.1 protruding the support body 1.2 in the initial position I. The needle shield 1.1 is releasably retained in the initial position I by the guide pin 1.1.2 that is located in a start position PI corresponding to the initial position I within the guide track 1.2.4.

The guide pin 1.1.2 in the start position PI abuts a first U-shaped indentation 1.2.4.1 in the distal direction and in a lateral direction L perpendicular to the central axis A, so that the guide pin 1.1.2 is prevented from leaving the start position PI in both the distal and in the lateral direction L. The guide pin 1.1.2 in the start position PI further abuts an inclined camming surface 1.2.4.2 in a proximal direction.

When the needle shield 1.1 is slid relative to the support body 1.2, the guide pin 1.1.2 moves within and along the guide track 1.2.4.

A generally L-shaped cut-out is 1.2.5 formed into the support body 1.2 adjacent to the guide track 1.2.4. The cut-out 1.2.5 allows a side wall 1.2.6 of the guide track 1.2.4 to be deflected in the lateral direction L. The generally L-shaped cut-out 1.2.5 comprises an axial section 1.2.5.1 that extends parallel to a first section 1.2.4.3 of the guide track 1.2.4 and parallel to the central axis A of the safety device 1. A lateral section 1.2.5.2 of the cut-out 1.2.5 is oriented at angle of approximately 90 degrees relative to the central axis A. The lateral section 1.2.5.2 of the cut-out 1.2.5 connects the cut-out 1.2.5 with the guide track 1.2.4.

Alternatively, the cut-out 1.2.5 may be separated from the guide track 1.2.4 by a separating wall of reduced strength that acts as a predetermined breaking point that creates an audible sound when the flexible side wall 1.2.6 is deflected.

As can be seen in the sectional view of FIG. 2, a compression spring 1.4 is arranged within the support body 1.2 that bears proximally against the inner surface 1.2.3 of the support body 1.2 and distally against an interior surface formed to the needle shield 1.1, whereby needle shield 1.1 and support body 1.2 are biased away from each other. The compression spring 1.4 is in a partially compressed and thus partially energized state when the needle shield 1.1 is in the initial position I.

FIG. 4 shows a sectional view of the safety device 1 with the needle shield 1.1 in the retracted position II. The section plane of FIG. 4 is rotated around the central axis A by an angle of 90 degrees relative to the section plane shown in FIG. 2. The needle shield 1.1 in the retracted position II is substantially received within the support body 1.2, so that the hypodermic needle 2.1 protrudes the skin-contact flange 1.1.1 in the distal direction. An inner rib 1.2.7 is formed to an interior surface of the support body 1.2 that protrudes in a radial inward direction. The needle shield 1.1 in the retracted position II abuts the inner rib 1.2.7, so that the needle shield 1.1 is retractable into the support body 1.2 by an axial length that is limited by the inner rib 1.2.7. Thus, the hypodermic needle 2.1 protrudes the skin-contact flange 1.1.1 distally by a distance that defines a penetration depth of the hypodermic needle 2.1 during the injection, whereas the penetration depth is limited by the inner rib 1.2.7.

The compression spring 1.4 is compressed and energized when the needle shield 1.1 is in the refracted position II. The closed proximal end of the outer body 1.3 abuts a proximal end of the piston rod 2.5, so that the piston 2.4 can be moved in the distal direction by actuating the outer body 1.3 and pushing the outer body 1.3 in the distal direction.

Alternatively, the piston rod 2.5 is connected to the outer body 1.3 or integral to the outer body 1.3. This alternative embodiment has additional advantage of a low overall part count, so that manufacturing costs are reduced.

FIG. 5 shows a sectional view of the injection device D, wherein the needle shield 1.1 of the safety device 1 is retained in an advanced position III. The needle shield 1.1 is in the advanced position III protruding the support body 1.2 in the distal direction and surrounding the hypodermic needle 2.1 of the pre-filled syringe 2 received within the safety device 1. The needle shield 1.1 has been moved to the advanced position III by the action of the relaxing compression spring 1.4.

The support body 1.2 is substantially received within the outer body 1.3 at the end of the injection stroke. The locking catch 1.3.2.1 of the clamp arm 1.3.2 protrudes into the locking recess 1.2.2 of the support body 1.2 to irreversibly lock the outer body 1.3 relative to the support body 1.2. Thus, a subsequent movement of the outer body 1.3 relative to the support body 1.2 is prevented.

Figure 6:
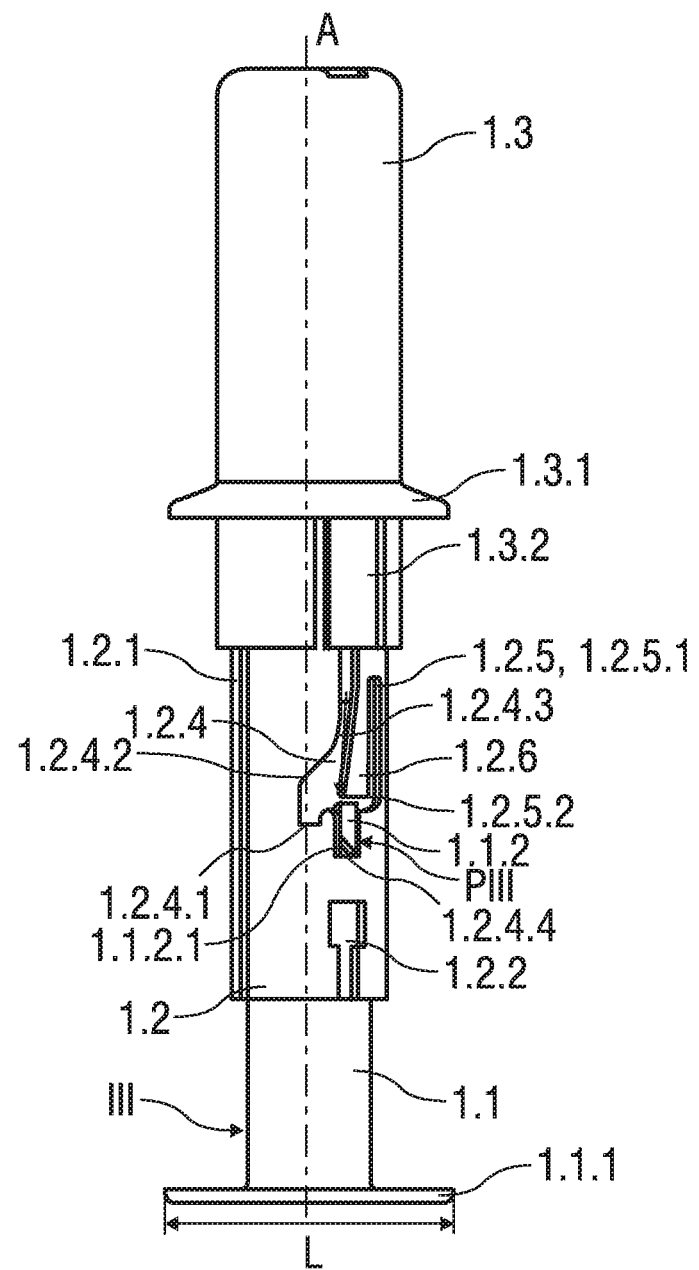
FIG. 6 shows a side view of an injection device with a safety device, wherein a needle shield is retained in an advanced position

As can be seen in FIG. 6, the needle shield 1.1 is permanently retained and locked to the advanced position III after a single use of the safety device 1. When the needle shield 1.1 is in the advanced position III, the guide pin 1.1.2 integral to the needle shield 1.1 is retained in an end position PIII located at a distal end of the guide track 1.2.4. The guide pin 1.1.2 in the end position PIII abuts a second U-shaped indentation 1.2.4.4 in both the lateral direction L and in the distal direction. Furthermore, the guide pin 1.1.2 in the end position PIII abuts a distal end of the side wall 1.2.6, so that any rotational or translatory movement of the needle shield 1.1 in the advanced position III is prevented by the guide pin 1.1.2 interacting with the guide track 1.2.4 in the end position PIII.

Before the injection, the guide pin 1.1.2 is retained in the start position PI shown in FIG. 3, whereby the needle shield 1.1 is retained in the corresponding initial position I.

The injection is carried out by orientating the central axis A essentially perpendicular to the skin of the patient, whereas the skin-contact flange 1.1.1 of the needle shield 1.1 rests on the skin surface of the patient and the proximal section of the outer body 1.3 proximal of the hand flange 1.3.1 is gripped by the user performing the injection. The hand flange 1.3.1 supports the hand of the user to push the outer body 1.3 towards the skin surface of the patient.

In a first stage of the injection, the needle shield 1.1 is pushed inside the support body 1.2, whereby the hypodermic needle 2.1 is exposed to penetrate the skin of the patient and the compression spring 1.4 is compressed and charged. The guide pin 1.1.2 is pushed against an inclined camming surface 1.2.4.2 and leaves its start position PI indicated by the arrow in FIG. 3 in a direction oriented at an acute angle relative to the central axis A, whereby the needle shield 1.1 changes an angular orientation relative to the support body 1.2 and rotates within the support body 1.2 around the central axis A about an angle of a few degrees.

A soon as the guide pin 1.1.2 leaves the start position PI, the safety features of the safety device 1 that provide needle safety and prevent re-usage of the device are activated. The safety device 1 is designed to become needle safe upon removal of the skin-contact flange 1.1.1 from the injection site at any stage of the medication delivery.

The needle shield 1.1 is pushed further proximally, so that the guide pin 1.1.2 moves proximally along the guide track 1.2.4 until the needle shield 1.1 abuts the inner rib 1.2.7, as illustrated in FIG. 4. The hypodermic needle 2.1 penetrates the skin of the patient. The penetration depth, which is defined as an axial length that a distal tip of the hypodermic needle 2.1 protrudes the skin-contact flange 1.1.1 in the distal direction, is set and limited by the inner rib 1.2.7 abutting the needle shield 1.1. The needle shield 1.1 is in the retracted position II when the guide pin 1.1.2 reaches a corresponding intermediate position PII, as indicated in FIG. 3 by a contour. The intermediate position PII is located at a proximal end of the first section 1.2.4.3 of the guide track 1.2.4.

When the needle shield 1.1 is in the retracted position II the compression spring 1.4 disposed in the support body 1.2 is compressed and fully energized. Consequently, the needle shield 1.1 in the retracted position II is biased by the compression spring 1.4 in the distal direction. A user performing the injection exerts a force in the distal direction towards the skin surface of the patient to keep the needle shield 1.1 in the retracted position II.

In the second stage of the injection, the outer body 1.3 is pushed in the distal direction towards the skin of the patient. The proximal end of the outer body 1.3 abuts the piston rod 2.5, so that the piston 2.4 is distally moved within the inner cavity 2.3.1 and the medication is expelled through the hypodermic needle 2.1 beneath the skin of the patient. As shown in FIG. 5, the locking catch 1.3.2.1 engages the locking recess 1.2.2 of the support body 1.2 at the end of the injection stroke, whereby the outer body 1.3 is irreversibly locked to the support body 1.2 preventing a subsequent use of the safety device 1.

The clamp arm 1.3.2 with the locking catch 1.3.2.1 is initially retained in a hole profile (not illustrated) at the beginning of the injection. A force required for the locking catch 1.3.2.1 to exit the hole profile exceeds the force required to move the needle shield 1.1 in the proximal direction, so that, at the beginning of the injection, the needle shield 1.1 first moves proximally to expose the needle, and, after the needle has been exposed, the outer body 1.3 moves distally to expel the medication. The interaction of the locking catch 1.3.2.1 thus ensures the stage-wise actuation of the injection.

As soon as the injection device D is removed from the skin surface of the patient, the compression spring 1.4 relaxes and moves the needle shield 1.1 in the distal direction towards the advanced position III. The guide pin 1.1.2 jointly moves with the needle shield 1.1 within the guide track 1.2.4 from the intermediate position PII towards the end position PIII, as indicated by the arrow in FIG. 6, whereby the side wall 1.2.6 of the guide track 1.2.4 is laterally deflected.

Upon entering the end position III, the tapered end 1.1.2.1 of the guide pin 1.1.2 abuts an arcuate section 1.2.4.5 of the guide track 1.2.4, so that the guide pin 1.1.2 is redirected in the lateral direction L. At the same time, the guide pin 1.1.2 pushes against the side wall 1.2.6 in the lateral direction L, whereby the side wall 1.2.6 is laterally deflected, so that the guide pin 1.1.2 is allowed to enter the end position PIII.

As the guide pin 1.1.2 enters the end position PIII, the needle shield 1.1 slightly changes its angular orientation relative to the support body 1.2 and rotates within the support body 1.2 around the central axis A about an angle of a few degrees.

When the guide pin 1.1.2 reaches the end position PIII located at a distal end of the guide track 1.2.4, the side wall 1.2.6 resiliently snaps back into place and blocks a subsequent proximal movement of the guide pin 1.1.2. Furthermore, a lateral movement of guide pin 1.1.2 is blocked in the end position PIII of the guide track 1.2.4 by the second U-shaped indentation 1.2.4.4. The needle shield 1.1 is thus permanently retained in and irreversibly locked to the advanced position III, so that the hypodermic needle 2.1 is protected from re-exposure.

FIGS. 7A to 7D show exploded views of alternative embodiments for the safety device 1 that are within the scope of the present invention.

FIG. 7A shows schematically the design of the safety device 1 substantially described herein above.

FIG. 7B shows an alternative embodiment, wherein the guide track 1.2.4 is formed into the needle shield 1.1 and the guide pin 1.1.2 is formed to an inner surface of the support body 1.2. The guide pin 1.1.2 protrudes from the inner surface of the support body 1.2 in a radial inward direction.

FIGS. 7C and 7D show alternative embodiments, wherein the needle shield 1.1 has an inner diameter that is sized to receive the support body 1.2. The support body 1.2 slides into the needle shield 1.1 when the needle shield 1.1 is moved from the initial position I to the retracted position II.

FIG. 7D shows an alternative embodiment, wherein the guide track 1.2.4 is formed into support body 1.2 and the guide pin 1.1.2 is formed to an inner surface of the needle shield 1.1. The guide pin 1.1.2 protrudes from the inner surface of the support body 1.2 in a radial inward direction.

The safety device 1 presented herein above has a low number of parts and comprises only three parts preferably made from a plastics material: the support body 1.2, the outer body 1.3 and the needle shield 1.1. The safety device 1 provides a simple mechanism to avoid needle stick injuries. The injection is carried out by a single movement of the outer body 1.3 towards the skin of the patient, whereby the safety features providing needle safety are automatically activated. During the injection, the needle shield 1.1 rotates within and relative to the support body 1.2.

The invention claimed is:
1. A safety device for a pre-filled syringe, comprising:
   a hollow support body to retain the pre-filled syringe therein,
   a hollow needle shield that is slidable relative to the support body, and
   a guiding mechanism for guiding movement of the needle shield relative to the support body, wherein the guiding mechanism comprises a guide pin, a guide track, and a cut-out adjacent to the guide track,
   wherein the guide pin protrudes into the guide track and is configured to move within and along the guide track when the needle shield is slid relative to the support body,
   wherein the cut-out allows a side wall of the guide track to be deflected in a lateral direction perpendicular to a central axis of the safety device,
   wherein the guide track comprises a U-shaped indentation located at a distal end of the guide track, and the U-shaped indentation is shaped to permanently retain the guide pin in an end position in which the guide pin abuts the U-shaped indentation in a distal direction and in the lateral direction and a distal end of the side wall in a proximal direction so that the guide pin is locked to the end position, and wherein the side wall of the guide track is configured to laterally deflect when the guide pin enters the end position.

2. The safety device according to claim 1, wherein the guide pin extends from either the needle shield or the support body in a radial direction and the guide track is formed into the other of the needle shield or the support body.

3. The safety device according to claim 1, wherein an axial section of the cut-out extends parallel to a first section of the guide track and parallel to the central axis.

4. The safety device according to claim 1, wherein the guide pin is integrally formed to an outer surface of the needle shield.

5. The safety device according to claim 1, wherein the needle shield is rotatable relative to the support body when the needle shield is moved from an initial position to a retracted position or from the retracted position to an advanced position by movement of the guide pin along the guide track.

6. The safety device according to claim 1, wherein the guide track comprises another U-shaped indentation shaped to retain the guide pin in a start position, and the guide pin in the start position abuts the other U-shaped indentation of the guide track in the distal direction and in the lateral direction and an inclined camming surface in the proximal direction.

7. The safety device according to claim 1, wherein the guide pin comprises a tapered end to abut an arcuate section of the guide track to redirect the guide pin into the end position.

8. The safety device according to claim 1, wherein the needle shield comprises a skin-contact flange.

9. The safety device according to claim 1, wherein the needle shield is retractable into the support body from an initial position to a retracted position, in which the needle shield protrudes from the support body by an axial length that is limited by an inwardly protruding inner rib of the support body.

10. The safety device according to claim 1, wherein the support body is retained within and slidable with respect to an outer body in the distal direction, the outer body comprising at least one locking catch to engage a locking recess formed into the support body to irreversibly lock the outer body relative to the support body when the support body is substantially received within the outer body.

11. An injection device comprising:
a pre-filled syringe, and
a safety device comprising
a hollow support body to retain the pre-filled syringe therein,
a hollow needle shield that is slidable relative to the support body, and
a guiding mechanism for guiding movement of the needle shield relative to the support body, wherein the guiding mechanism comprises a guide pin, a guide track, and a cut-out adjacent to the guide track,
wherein the guide pin protrudes into the guide track and is configured to move within and along the guide track when the needle shield is slid relative to the support body,
wherein the cut-out allows a side wall of the guide track to be deflected in a lateral direction perpendicular to a central axis of the safety device,
wherein the guide track comprises a U-shaped indentation located at a distal end of the guide track, and the U-shaped indentation is shaped to lock the guide pin in an end position in which the guide pin abuts the U-shaped indentation in a distal direction and in the lateral direction and a distal end of the side wall in a proximal direction, and
wherein the side wall of the guide track is configured to laterally deflect when the guide pin enters the end position.

12. The injection device according to claim 11, wherein a penetration depth of the pre-filled syringe is limited by an inner rib of the support body when the needle shield is in a retracted position.

13. An injection kit comprising:
an injection device comprising
a pre-filled syringe, and
a safety device comprising
a hollow support body to retain the pre-filled syringe therein,
a hollow needle shield that is slidable relative to the support body, and
a guiding mechanism for guiding movement of the needle shield relative to the support body, wherein the guiding mechanism comprises a guide pin, a guide track, and a cut-out adjacent to the guide track,
wherein the guide pin protrudes into the guide track and is configured to move within and along the guide track when the needle shield is slid relative to the support body,
wherein the cut-out allows a side wall of the guide track to be deflected in a lateral direction perpendicular to a central axis of the safety device,
wherein the guide track comprises a U-shaped indentation located at a distal end of the guide track, and the U-shaped indentation is shaped to lock the guide pin in an end position in which the guide pin abuts the U-shaped indentation in a distal direction and in the lateral direction and a distal end of the side wall in a proximal direction,
wherein the side wall of the guide track is configured to laterally deflect when the guide pin enters the end position; and
a substantially tubular needle cap remover that is insertable into the needle shield from a distal end and is clampable to a needle cap frictionally affixed to a distal end of the pre-filled syringe.

14. The injection device according to claim 11, wherein the guide pin extends from either the needle shield or the support body in a radial direction and the guide track is formed into the other of the needle shield or the support body.

15. The injection device according to claim 11, wherein an axial section of the cut-out extends parallel to a first section of the guide track and parallel to the central axis.

16. The injection device according to claim 11, wherein the guide pin is integrally formed to an outer surface of the needle shield.

17. The injection kit according to claim 13, wherein the guide pin extends from either the needle shield or the support body in a radial direction and the guide track is formed into the other of the needle shield or the support body.

18. The injection kit according to claim 13, wherein an axial section of the cut-out extends parallel to a first section of the guide track and parallel to the central axis.

19. The injection kit according to claim 13, wherein the guide pin is integrally formed to an outer surface of the needle shield.

20. The safety device according to claim 1, wherein the U-shaped indentation is shaped to abut the guide pin in a first lateral direction, a second lateral direction, and the distal direction.

* * * * *